United States Patent [19]

Bohl

[11] Patent Number: 4,617,277
[45] Date of Patent: Oct. 14, 1986

[54] PROCESS AND APPARATUS FOR MONITORING AMBIENT CARBON MONOXIDE

[75] Inventor: Thomas L. Bohl, Madison, Ohio

[73] Assignee: The Babcock & Wilcox Company, New Orleans, La.

[21] Appl. No.: 592,510

[22] Filed: Mar. 23, 1984

[51] Int. Cl.$^4$ .................. G01N 21/78; G01N 31/22
[52] U.S. Cl. ........................... 436/34; 356/402; 356/445; 364/525; 364/579; 422/66; 422/87; 436/44; 436/134; 436/169
[58] Field of Search ............. 422/56, 57, 86, 87, 422/66; 436/134, 169, 44, 34; 364/525, 526, 579, 497, 498, 499; 356/445, 402

[56] References Cited

U.S. PATENT DOCUMENTS

| | | | |
|---|---|---|---|
| 2,111,301 | 3/1938 | Schroter | 436/134 |
| 2,153,568 | 4/1939 | Johnson | 436/134 X |
| 2,812,243 | 11/1957 | Goody | 422/87 |
| 4,023,930 | 5/1977 | Blunck et al. | 422/87 X |
| 4,050,895 | 9/1977 | Hardy et al. | 422/86 X |
| 4,115,067 | 9/1978 | Lyshlow | 422/87 X |
| 4,181,699 | 1/1980 | Kitzinger | 422/87 |
| 4,203,156 | 5/1980 | Ishikawa | 364/579 X |

FOREIGN PATENT DOCUMENTS 1523141  5/1969  Fed. Rep. of Germany ........ 422/87

Primary Examiner—Arnold Turk
Attorney, Agent, or Firm—Vytas R. Matas; Robert J. Edwards

[57] ABSTRACT

A system for monitoring ambient carbon monoxide. Light from a source (14) is directed against a measuring element (10) which darkens in color as it absorbs carbon monoxide. The light reflected from the element is received by a photocell (16) which generates an electrical signal proportional to the intensity of the reflected light received thereby. The signal is sampled periodically, and stored in a microprocessor (24) which computes the rate of change of the signals. The periodic measurement of the intensity of the light can be varied in response to the rate of change of the light intensity measurement. When the rate of change reaches a level indicative of an unsafe level of ambient carbon monoxide, an alarm (34) is energized. Light from the source is simultaneously directed against a reference element (12) with the light reflected therefrom being received by a photocell (18) which generates an electrical signal proportional to the intensity of the light received thereby. A comparator (30) compares the electrical signal generated by the photocells and energizes an indicator (32) when the comparison indicates that the measuring element has absorbed sufficient carbon monoxide to require that the element be replaced.

11 Claims, 3 Drawing Figures

PROCESS AND APPARATUS FOR MONITORING AMBIENT CARBON MONOXIDE

TECHNICAL FIELD

The present invention relates to ambient gas monitoring, and more particularly to a system for continuously monitoring the level of ambient carbon monoxide.

BACKGROUND ART

As more and more emphasis is put on energy conservation, homes and workplaces are being more tightly sealed than in the past in order to minimize heat losses. As sealing is improved, there is also less opportunity for the dilution and escape of any toxic gases, which could result from malfunctioning or misadjusted heating units or the like. Of particular interest in the home or normal workplace environment is the buildup of carbon monoxide.

There are a number of known ways to measure carbon monoxide, including volumetric chemical absorption, catalytic heat of reaction, spectroscopy, thermal conductivity, and surface absorption semiconductors. Volumetric chemical absorption is typified by the well-know Orsat analyzers, however, these are not capable of being automated for continuous sampling. Devices which operate on the principles of catalytic heat of reaction, spectroscopy and thermal conductivity can provide continuous analysis, however, they tend to lack sensitivity, are relatively expensive, and have relatively high power consumption to be practical for continuous household use. Surface absorption devices meet most of the requirements for household and workplace use, however, they also respond to many commonly used non-toxic substances such as hair sprays and other aerosol products, and are thus considered to be impracticable.

Because of the foregoing, it has now become desirable to develop a carbon monoxide monitor which is practical for continuous use in the home or workplace.

SUMMARY OF THE INVENTION

The present invention solves the aforementioned problems associated with knownprior art devices, as well as other problems, by providing an analyzer of the chemical absorption type using chemicals in solid or gel form wherein the reaction with carbon monoxide (CO) produces a color change which is continuously measured. In general principles, the invention is similar to the Orsat analyzer, however, the use of solid or gel form chemicals as opposed to liquids permits the use of small, relatively inexpensive components which are reliable and which can be designed for minimal power consumption.

More specifically, the measuring element of the present invention is made from a chemical formulation which changes color upon exposure to CO, with the rate of change of color being proportional to the level of CO exposure per unit time. The color change is irreversible, thus the device essentially totalizes the CO exposure. The chemical, in solid or gel form, defines a measuring element disposed adjacent a reference element which is permanently colored to match the color of the measuring element at the end of its useful life. A pair of light beams are directed at the measuring and reference elements and reflected to a pair of photocells. The light from the two elements is used to generate electrical signals proportional to the light intensities. By means of a microprocessor, these intensity signals are compared to each other to generate an indication that the measuring element must be changed, and the measuring element signal is compared with a previous measuring element signal, the rate of change from one signal to the next being used as an indication of an unsafe level of CO in the atmosphere, whereby a rate exceeding a predetermined value will energize an alarm.

DESCRIPTION OF THE PREFERRED EMBODIMENT

Figure 1:
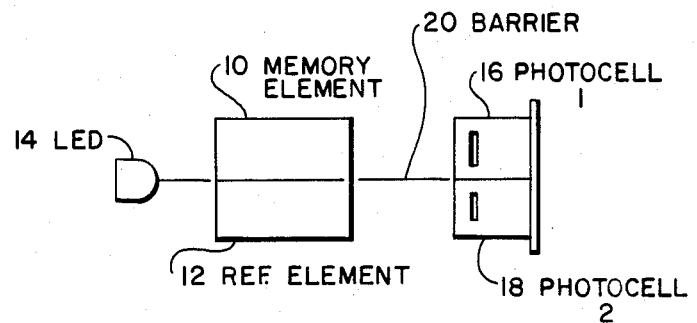
FIG. 1 is a plan view of the invention.
Figure 2:
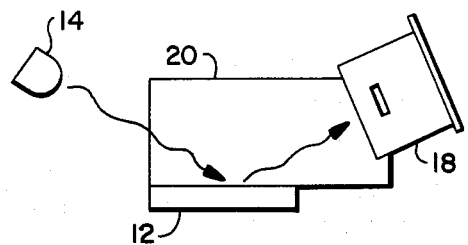
FIG. 2 is a side elevation view of the invention.

Referring now to the drawings where the illustrations are for the purpose of describing the preferred embodiment and are not intended to limit the invention hereto, FIG. 1 is a plan view of the present invention, comprising a measuring element 10, a reference element 12, a light source 14, first and second photocells 16 and 18, and a light barrier 20 disposed between the measuring and reference elements and between the photocells.

The measuring element 10 is made from a chemical formulation which changes color upon exposure to CO. An example of such a formulation is as follows:
 100 gm. water
 10 gm. sodium chloride
 0.5 gm. palladium II chloride
 2 gm. sodium acetate A solid is made by dispensing the above solution on powdered silica gel. A shaped structure is then made by mixing the activated silica gel with a suitable porous binder which can be pelletized. An alternate chemical is an aqueous solution of potassium tetrachloropalladate applied to an absorbant such as silica gel, as in the first compound.

The resulting reaction of these compounds produces a change in color from light tan to dark brown or black upon exposure to CO.

Referring to FIG. 1, visible light from source 14, such as an LED or other low power device, is directed simultaneously as shown to the measuring element 10 and the reference element 12. The measuring element is formulated from one of the chemical compounds described above, or another suitable compound which is capable of producing the desired color change upon exposure to CO, while the reference element is an inert material, such as a common plastic, which is permanently colored to match the color which the measuring element will attain when it reaches the end of its useful life and must be changed.

The light source 14 and the measuring and reference elements are initially adjusted so that the light impinging on the two elements is approximately equal. The barrier 20 separates the light reflected from the elements into two independent beams, each impinging on a photocell, with light reflected from the measuring element 10 impinging on photocell 16, and light reflected from the reference element 12 impinging on photocell 18. As is well known, light received by each photocell generates an electrical signal which is proportional to the intensity of the light received by that cell.

Figure 3:
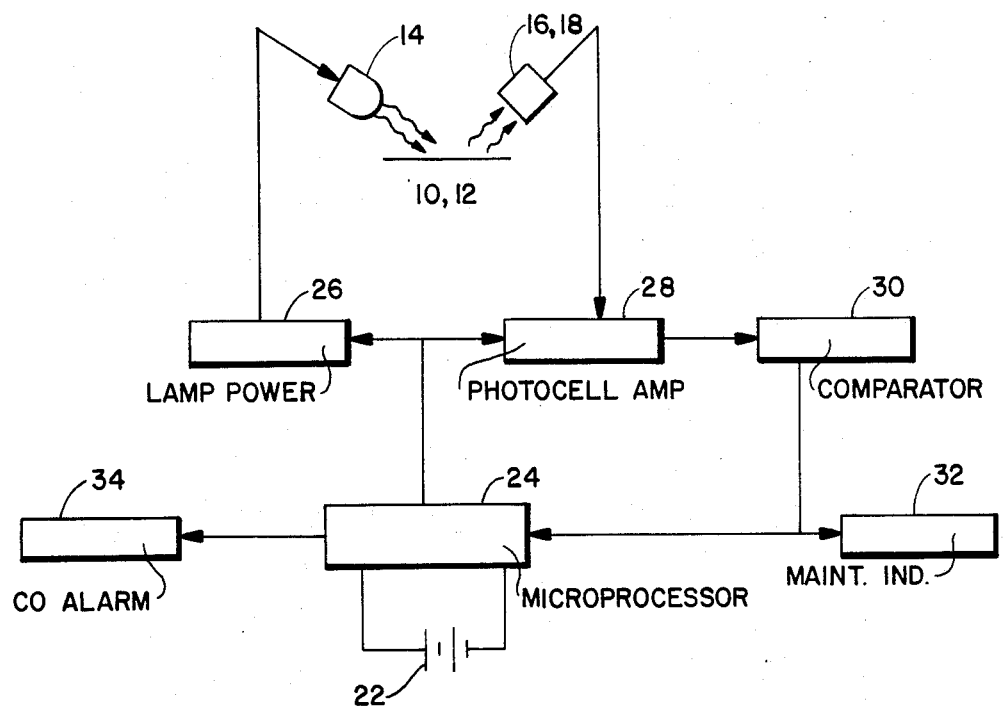
FIG. 3 is a schematic diagram of the invention.

FIG. 3 is a schematic diagram illustrating the monitoring system of the present invention. The circuit comprises a battery 22 which provides power to a microprocessor 24. The microprocessor includes outputs to a power unit 26 for operating the light source 14, and to a photocell amplifier 28. The amplifier provides output signals proportional to the intensity of light sensed by each of the photocells to a comparator 30 which provides an output signal proportional to the difference between the light intensities sensed by the photocells. This latter output signal is applied as an input signal to a maintenance indicator 32 and to the microprocessor 24.

If the measuring signal is less than or equal to the reference signal, that is if the measuring element 10 reaches its maximum darkness, a suitable alarm will be energized at the maintenance indicator 32 to indicate that the measuring element must be changed.

Since the color change of the measuring element represents an accumulation of CO exposure over a period of time, means must be provided to detect an instantaneous unsafe CO level rather than the end result of constant exposure to CO, which may alwa be at a safe level. It can be appreciated that the comparison of the outputs of the photocells 16 and 18 detects only the accumulated CO level.

In accordance with the invention, only the microprocessor and a minimum number of supporting components are engaged continuously, i.e. the means for periodically sampling the signal. At intervals prescribed by the microprocessor, e.g., once each five minutes, the light source 14 and the rest of the circuit are energized for a few seconds. During this time interval, signals from the photocells are processed as described above to determine the condition of the measuring element.

The signal from the photocell 16 associated with the measuring element 10 is also compared with its last previous signal stored by the microprocessor. If the comparison shows that the signal has increased, indicating an increased CO level, the microprocessor decreases the "off" time of the system by an amount proportional to the signal change. If the difference between the instant and previous signals continues to increase, the "off" time will continue to be decreased until at some predetermined cycle rate corresponding to an unsafe CO level, an alarm 34 will be energized. The actual cycle time which will cause the alarm to be energized will depend at least in part on the particular chemical formulation used for the measuring element.

If succeeding signals are equal or are different by less than a predetermined threshold level, the microprocessor will slow the cycle time back to its normal frequency.

Certain modifications and improvements will occur to those skilled in the art upon reading the foregoing description. It will be understood that all such improvements and modifications have been deleted herein for the sake of conciseness and readability, but are properly within the scope of the following claims.

We claim:

1. Apparatus for intermittently monitoring ambient carbon monoxide comprising; a measuring element which undergoes color change upon exposure to carbon monoxide; a light source for periodically directing light against said measuring element; first photoresponsive means receiving light reflected from said measuring element, said first photoresponsive means providing a first electrical signal proportional to the intensity of light reflected from said measuring element; and microprocessor means including means for periodically actuating said light source and sampling said first electrical signal, means for comparing said sampled signal with a previous first electrical signal, means for computing the rate of change of said first electrical signal and means for increasing or decreasing the period of said periodic actuation means in response to the rate of change of said computing.

2. Apparatus as claimed in claim 1, in which said measuring element comprises a material which absorbs carbon monoxide, the cumulative absorption of carbon monoxide causing said measuring element to darken in color.

3. Apparatus as claimed in claim 2, in which said measuring element comprises a chemical formulation which includes water, sodium chloride, palladium II chloride and sodium acetate.

4. Apparatus as claimed in claim 2, in which said measuring element comprises a chemical formulation including an aqueous solution of potassium tetrachloropalladate.

5. Apparatus as claimed in claim 1, including first alarm means energized when said rate of change reaches a predetermined value.

6. Apparatus as claimed in claim 1, including a reference element against which said light source is also directed; second photoresponsive means receiving light reflected from said reference element, said second photoresponsive means providing a second electrical signal proportional to the intensity of the light reflected from said reference element; and comparator means comparing said first and second electrical signals.

7. Apparatus as claimed in claim 3, including second alarm means energized when the difference between said first and second electrical signals reaches a predetermined value.

8. Apparatus as claimed in claim 6, in which said measuring element and said reference are disposed in side by side relationship in position to receive equal light from said light source, said first and second photoresponsive means are disposed in corresponding side by side relationship, and including separator means disposed between said measuring element and said reference element and between said first and second photoresponsive means to separate the light from said light source which is reflected from said measuring element from the light which is reflected from said reference element.

9. Apparatus as claimed in claim 6, in which said measuring element darkens with continued exposure to carbon monoxide, and in which said reference element is formed of an inert material colored to essentially match the color of said measuring element when said measuring element reaches a predetermined color.

10. A method for intermittently monitoring ambient carbon monoxide comprising the steps of providing a first element which changes color with exposure to carbon monoxide, periodically directing a beam of light against said first element, periodically measuring the intensity of light reflected from said first element, computing the rate of change of said light intensity measurements and varying the periodic measurement of the intensity of light in response to the rate of change of the light intensity measurement.

11. A method as claimed in claim 10, including simulataneously directing a beam of light against a second element of constant color, measuring the intensity of light reflected from said second element, and comparing the intensity of the light reflected from the first element with the light reflected from the second element.

* * * * *